(12) United States Patent
Sakami et al.

(10) Patent No.: US 8,147,130 B2
(45) Date of Patent: Apr. 3, 2012

(54) HEAT FLUX MEASUREMENT DEVICE FOR ESTIMATING FOULING THICKNESS

(75) Inventors: Mohamed Sakami, Clifton Park, NY (US); James Michael Storey, Houston, TX (US); Shobhana Mani, Houston, TX (US); Fulton Jose Lopez, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 686 days.

(21) Appl. No.: 12/105,320

(22) Filed: Apr. 18, 2008

(65) Prior Publication Data

US 2009/0262777 A1   Oct. 22, 2009

(51) Int. Cl.
*G01N 25/58* (2006.01)
*G01N 25/72* (2006.01)
*G01N 17/06* (2006.01)

(52) U.S. Cl. ............. 374/7; 374/134; 374/29; 374/137; 374/179

(58) Field of Classification Search ................. 374/4–7, 374/29, 30, 39, 40, 43–45, 100, 102, 103, 374/104, 110, 111, 112, 113, 115, 135, 137, 374/141, 148, 147, 166, 179, 208, 134, 34, 374/13, 10
See application file for complete search history.

(56) References Cited

U.S. PATENT DOCUMENTS

| | | | | |
|---|---|---|---|---|
| 3,232,113 A | * | 2/1966 | Malone | 374/30 |
| 3,417,617 A | * | 12/1968 | Rall | 374/165 |
| 3,605,490 A | * | 9/1971 | Progelhof et al. | 374/29 |
| 3,715,923 A | * | 2/1973 | Hornbaker et al. | 374/134 |
| 3,724,267 A | * | 4/1973 | Zoschak | 374/30 |
| 3,939,554 A | * | 2/1976 | Finney | 136/224 |
| 4,138,878 A | * | 2/1979 | Holmes et al. | 374/7 |
| 4,383,438 A | | 5/1983 | Eaton | |
| 4,521,864 A | * | 6/1985 | Characklis | 702/170 |
| 4,527,908 A | * | 7/1985 | Arisi | 374/147 |
| 4,839,593 A | * | 6/1989 | Spies | 324/240 |
| 5,086,204 A | * | 2/1992 | Liebert et al. | 219/69.17 |
| 5,215,704 A | * | 6/1993 | Hirota | 376/245 |
| 5,233,943 A | | 8/1993 | Martin et al. | |
| 5,314,247 A | * | 5/1994 | Liebert et al. | 374/29 |
| 5,399,017 A | * | 3/1995 | Droege | 374/7 |
| 6,062,069 A | * | 5/2000 | Panchal et al. | 73/53.01 |
| 6,220,750 B1 | * | 4/2001 | Palti | 374/164 |
| 6,238,087 B1 | * | 5/2001 | Burris et al. | 374/43 |
| 6,394,646 B1 | * | 5/2002 | Ringermacher et al. | 374/7 |
| 6,485,174 B1 | * | 11/2002 | Albrecht et al. | 374/29 |
| 6,499,876 B1 | * | 12/2002 | Baginksi et al. | 374/7 |
| 6,824,305 B1 | * | 11/2004 | Boyd et al. | 374/29 |
| 7,077,563 B2 | * | 7/2006 | Xiao et al. | 374/29 |
| 7,432,679 B2 | * | 10/2008 | Pronovost et al. | 318/471 |
| 7,607,825 B2 | * | 10/2009 | Koschack et al. | 374/7 |
| 2002/0099294 A1 | * | 7/2002 | Hamouda et al. | 600/474 |
| 2005/0217841 A1 | * | 10/2005 | Van Den Ende et al. | 165/287 |
| 2007/0025413 A1 | * | 2/2007 | Hays et al. | 374/7 |
| 2007/0081573 A1 | * | 4/2007 | Beardwood et al. | 374/7 |
| 2008/0163692 A1 | * | 7/2008 | Huang et al. | 73/627 |
| 2008/0291965 A1 | * | 11/2008 | Wolferseder | 374/7 |

(Continued)

*Primary Examiner* — Gail Verbitsky
(74) *Attorney, Agent, or Firm* — Ann M. Agosti

(57) ABSTRACT

A heat flux measurement device includes at least two thermocouples disposed within a front portion of the device at different axial distances from a front wall of the device. A correlation between the measured heat fluxes from the device over a period of time is used to estimate a fouling thickness on a wall, for example, a water wall of a radiant syngas cooler (RSC).

8 Claims, 4 Drawing Sheets

U.S. PATENT DOCUMENTS

| | | |
|---|---|---|
| 2008/0298426 A1* | 12/2008 | Koschack et al. .................. 374/7 |
| 2009/0192757 A1* | 7/2009 | Schwerer et al. ............. 702/130 |
| 2010/0020844 A1* | 1/2010 | Ashe ............................... 374/44 |
| 2010/0036638 A1* | 2/2010 | Friedrich et al. .............. 702/136 |
| 2010/0321046 A1* | 12/2010 | Randall et al. ................. 324/696 |
| 2011/0076207 A1* | 3/2011 | Tirio et al. ..................... 422/632 |
| 2011/0274138 A1* | 11/2011 | Auret et al. ..................... 374/45 |

* cited by examiner

US 8,147,130 B2

HEAT FLUX MEASUREMENT DEVICE FOR ESTIMATING FOULING THICKNESS

BACKGROUND

The invention relates in general to heat flux measurement devices, and in particular, to a temperature measurement device using at least two thermocouples to measure a heat flux at one side of a wall of a radiant syngas cooler (RSC) exposed to a gas stream and to estimate the fouling thickness on this same side of the wall.

In a coal gasification system, coal slurry from a feed pump and oxygen from an air separation plant are fed to a gasifier through a series of valves that operate in a carefully determined sequence to start the gasifier and provide positive isolation for shutdown. The oxygen and slurry combine in a feed injector that is designed to intimately mix and disperse the fuel and oxidant into the gasifier chamber.

The coal slurry and oxygen interact in the gasifier to produce three products: synthetic gas or "syngas," slag, and flyash. Syngas consists primarily of hydrogen ($H_2$), carbon monoxide (CO), water vapor, and carbon dioxide ($CO_2$), with smaller amounts of hydrogen sulfide ($H_2S$), carbonyl sulfide (COS), methane ($CH_4$), argon (Ar), and nitrogen ($N_2$). After moisture has been removed, the heating value of the syngas is about 250 BTU/SCF. It contains about 70% to about 75% of the heating value of the original fuel.

Coal and most other solid fuels contain some mineral matter that does not convert to syngas. Part of this mineral matter melts at the gasifier's elevated temperature and flows down the gasifier's refactory-lined walls. This material is called slag. It ultimately solidifies into an inert glassy frit with very little residual carbon content.

Some of the coal particles are not completely gasified; their contained volatile matter flashes off, and the residual carbon is only partially gasified, forming char particles. This char is referred to as "flyash," although its physical characteristics are quite different from conventional coal boiler flyash. Flyash particles contain a considerable amount of residual carbon plus the mineral matter from the coal particles. Flyash is transported out of the gasifier with the syngas.

In some configurations, the high temperature gasifier exit stream flows through a radiant syngas cooler (RSC), which is a high-pressure steam generator and gas cooler for improved efficiency and reliability. A typical RSC is shown generally at 100 in FIG. 6. Briefly stated, the radiant syngas cooler 100 is comprised of an outer shell 102 having an inlet at the upper end. A water bath 104 at the shell lower end receives a stream of a hot effluent comprised of produced syngas, together with entrained solids. Solid material is substantially removed from the effluent stream in the water bath. Any residual solids are then carried by cooled gas into a separation chamber or disengaging zone 106. The residual solids are thereafter conducted from the cooler by way of discharge port 108. A water wall 110 is spaced inwardly of the outer shell 102 for radiation and convection heat exchange with the hot syngas to the liquid circulated in the water wall tubes. The water wall 110 thereby defines an annulus or elongated annular chamber 112 with the inner wall of the shell 102.

As shown in FIG. 7, the water wall 110 is comprised of a plurality of circularly cavity heat conductive tubes 110a and 110b having a common manifold at the upper end which is communicated to a pressurized source of water. Functionally, the water provides a circulating heat transfer medium. The respective adjacent tubes 110a and 110b are connected one to the other, or joined by an intermediate webbing 114 to render the wall impervious to the hot effluent stream which is deposited into an internal chamber 116 of the water wall 110. A differential pressure sensing device 118 continuously monitors the differential pressure across water wall 110.

High pressure steam is generated inside the tubes 110a, 110b of the water wall 110 using circulating boiler feedwater. At the high temperatures, heat is transferred by radiation and convection. The syngas passes over the surface of the water bath 104 located at the bottom of the RSC 100 before exiting. The water bath 104 collects virtually all of the slag and about half of the flyash.

The water wall 110 also serves to protect the RSC's pressure containing shell 102 from the hot syngas. If a rupture of the water wall 110 does occur, outer shell 102 would be exposed to contact with excessively hot syngas. When the latter occurs, since the outer shell 102 is not constructed to safely contain the gas at the temperature and pressure at which it will be, the shell 102 is susceptible to being damaged and thermally stressed to the point where, if preventive measures at not taken, it will rupture.

The failure of the water wall 110 can occur from corrosion. Corrosive components in the syngas, such as hydrogen sulfide, can migrate into annulus 112, thereby exposing the external surface of water wall 110 to corrosion. The inner surface of shell 102 can also be exposed to these corrosive components.

Fouling is caused by the particles in the downwardly moving stream of syngas sticking to the relatively cooler walls of the RSC 100. Fouling is a major issue in the gasification process because it restricts flow, reduces heat transfer and substantially reduces operating efficiency of the RSC. Thus, there is a need to measure heat flux at the walls and to estimate the fouling thickness on the walls of the RSC.

BRIEF DESCRIPTION

Briefly, one aspect of the invention resides in a heat flux measurement device for estimating a fouling thickness on a wall over a period of time comprising a front portion having a front wall and an annular side wall defining a cavity; a first thermocouple disposed within the front portion at a first distance from the front wall for measuring a first temperature; and a second thermocouple disposed within the front portion at a second distance from the front wall for measuring a second temperature. The first and second temperatures are used to estimate a measured heat flux, and the measured heat flux is used to estimate a fouling thickness on a wall.

Another aspect of the invention resides in a method of estimating a fouling thickness on a wall over a period of time using a heat flux measurement device, comprising the steps of:

measuring a first temperature using a first thermocouple disposed within a front portion at a first distance from a front wall of the heat flux measurement device;

measuring a second temperature using a second thermocouple disposed within the front portion at a second distance from the front wall of the heat flux measurement device;

determining a heat flux based on the measured temperatures from the first and second thermocouples; and estimating a fouling thickness on a wall based on the determination of a variation in the heat flux.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
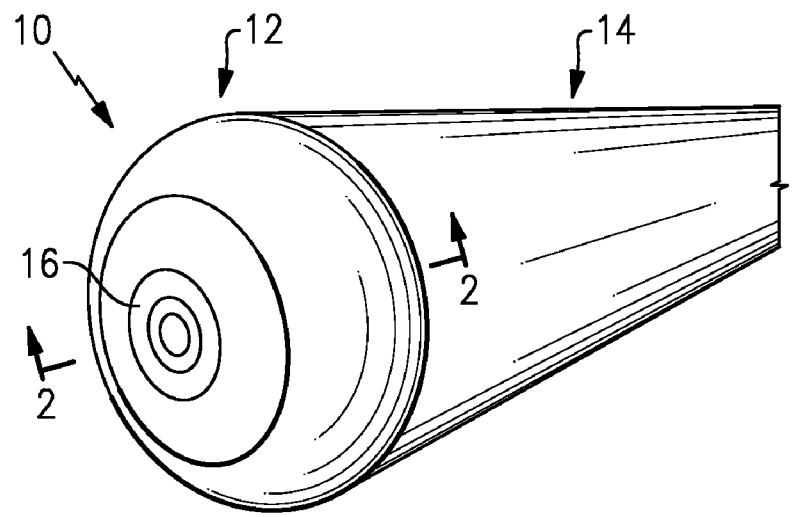
FIG. 1 is a perspective view of a temperature measurement device for estimating a fouling thickness in a radiant syngas cooler (RSC) according to an embodiment of the invention.
Figure 2:
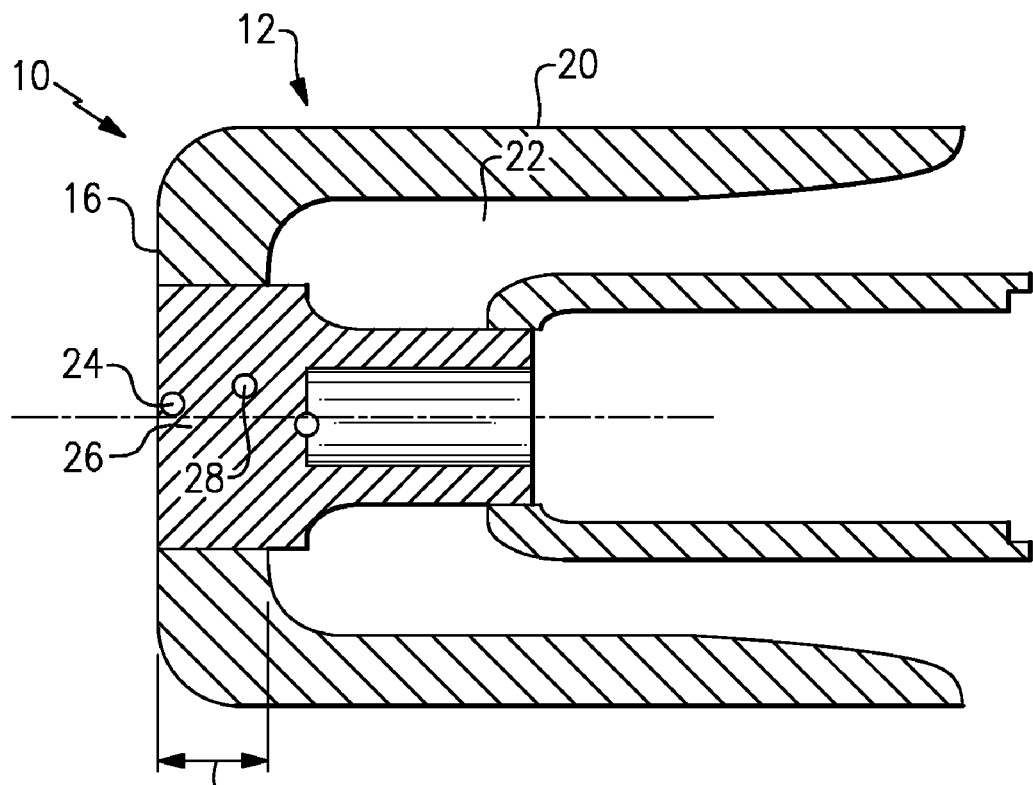
FIG. 2 is an enlarged, partial cross-sectional side view of the temperature measurement device taken along line 2-2 of FIG. 1.
Figure 3:
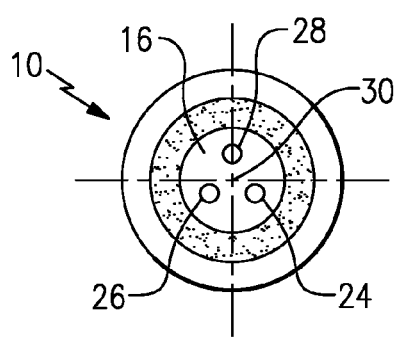
FIG. 3 is a cross-sectional view of the temperature measurement device illustrating the radial offset locations of the thermocouples.
Figure 7:
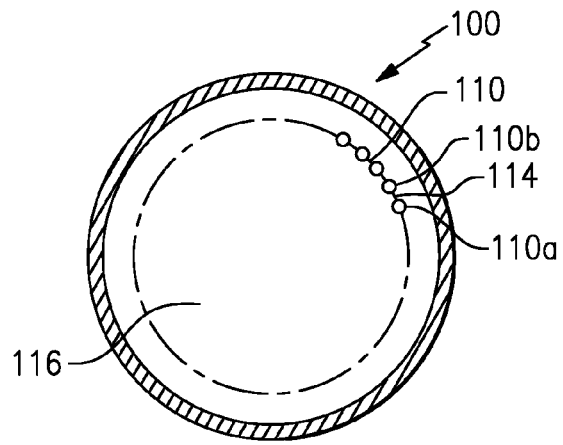
FIG. 7 is a cross-sectional view taken along line 7-7 of the RSC of FIG. 6.
Figure 6:
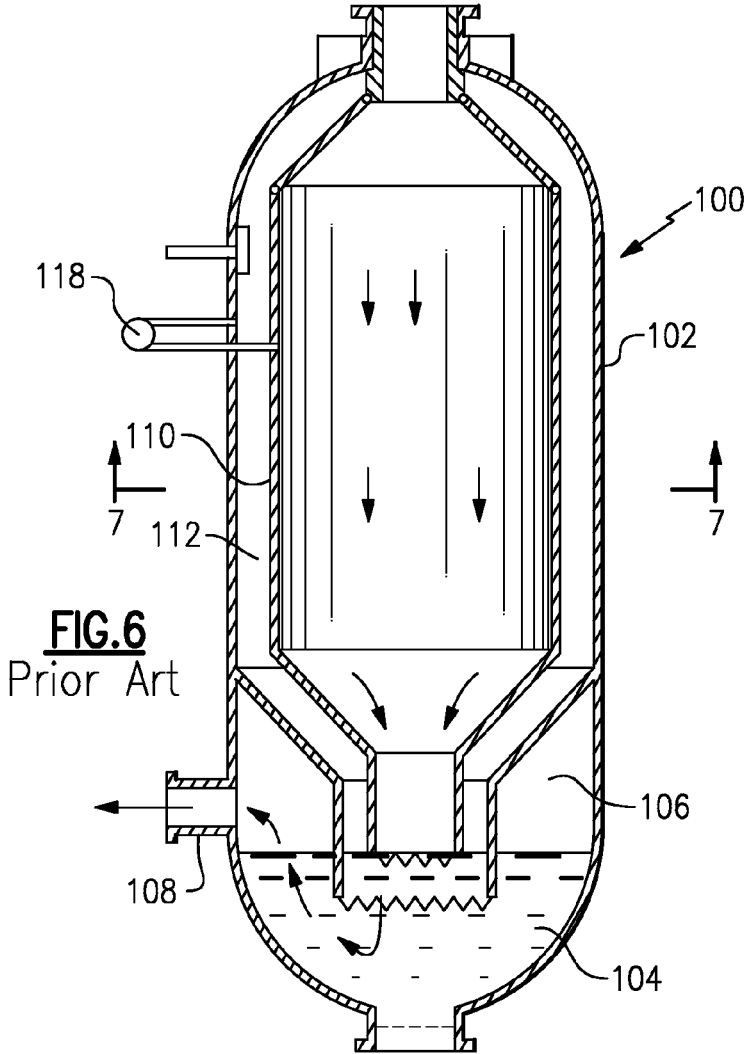
FIG. 6 is a cross-section, elevation view of a conventional radiant syngas cooler (RSC)

Referring now to FIGS. 1-3, a heat flux measurement device is shown generally at 10 according to an embodiment of the invention. In general, the device 10 comprises a heat flux probe that can be carried by any arbitrary shaped material. In the RSC application, a lance which is substantially cylindrical-shaped at the front portion 12 and elongated at the rear portion 14 was used. The heat flux probe 10 is made of a single piece of heat and corrosion resistant material, such as Inconel 600, and the like. The front portion 12 includes a front wall 16 having a thickness 18 and an annular side wall 20 defining a cavity 22 therein. A coolant, for example, saturated water circulating through the water wall 110 may be circulated through the cavity 22 to serve as a heat sink.

One aspect of the invention is that the front portion 12 of the heat probe 10 includes a plurality of thermocouples at different, predetermined locations from the front wall 16. In the illustrated embodiment, the heat probe 10 includes three thermocouples 24, 26 and 28 that are disposed within the front portion 12 at a different axial position from the front wall 16 of the heat probe 10, respectively. For example, the thermocouples 24, 26 and 28 can be located at a distance of about 0.10, 0.20 and 0.40 inches from the front wall 16. The thermocouples 24, 26 and 28 can be fixed into position by using any well-known means, such as brazing, and the like.

In addition, each thermocouple 24, 26 and 28 are at a different radial position with respect to a central, longitudinal axis 30 of the probe 10. In other words, the thermocouples 24, 26 and 28 are radially offset from each other so that they do not "shadow" each other, even though they are located at different axial distances from the front wall 16. It will be appreciated that the invention can be practiced with at least two thermocouples at any desired offset distance from the front wall and the central, longitudinal axis of the probe, and the invention is not limited by the total number of thermocouples and the distance from the front wall and the central, longitudinal axis. For example, the invention can be practiced with four or more thermocouples at different distances from the front wall of the probe.

Testing was performed by inserting the heat probe 10 through the water wall 110 and into the internal chamber 116 at two different elevations of the radiant syngas cooler (RSC) 100. Specifically, the heat probe 10 was positioned to measure both the temperature at the front side of the water tube 110$a$, 110$b$ (proximate the syngas) and two temperatures at a distance away from the front side. The testing was conducted to determine whether the temperature at the back wall of the water tube 110$a$, 110$b$ (proximate the water flowing through the water tube) would be constant with time and independent of the elevation of the heat probe 10 within the RSC 100.

Figure 4:
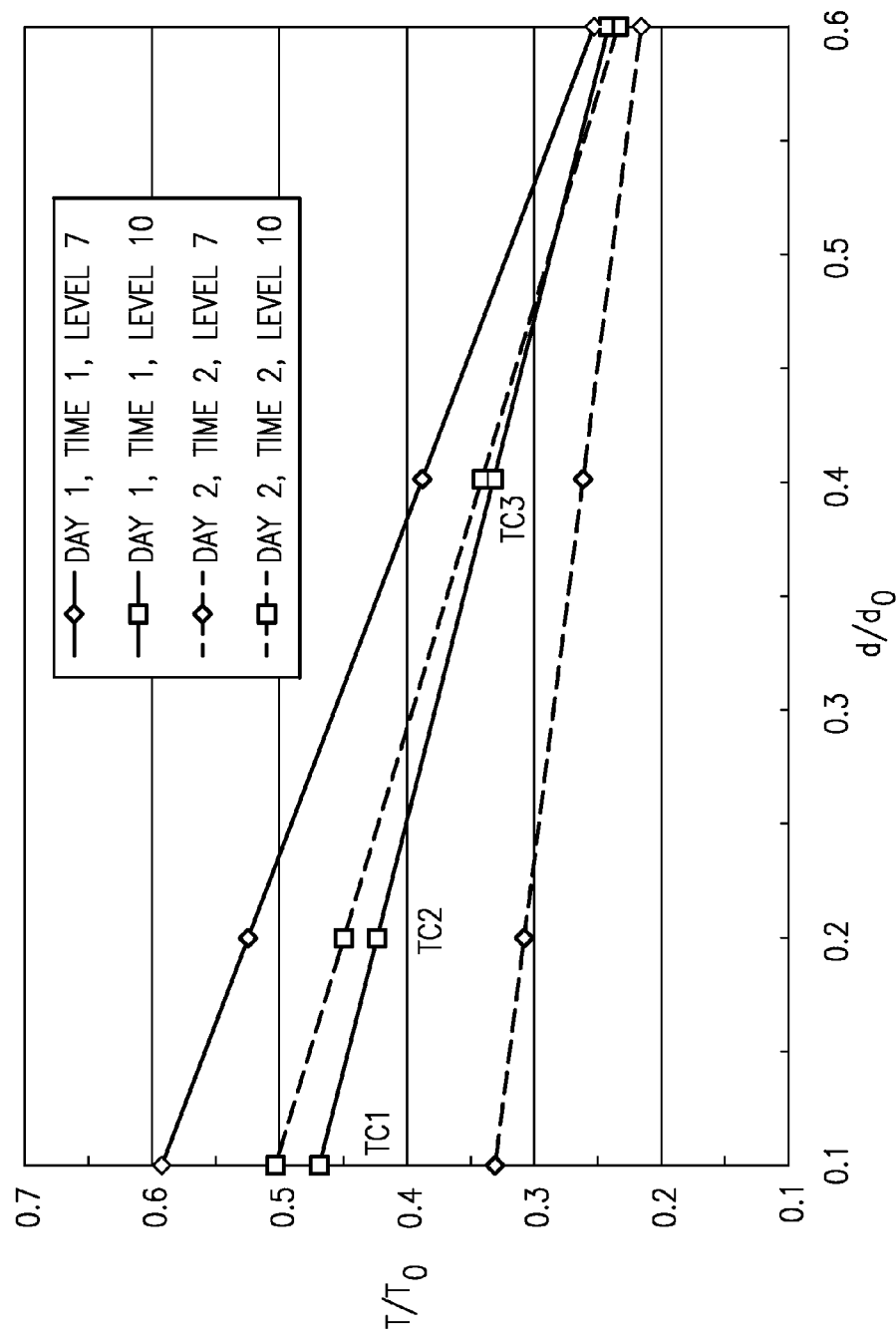
FIG. 4 is a graph illustrating the non-dimensional temperature measured by the heat flux probe by each thermocouple at two different elevations within the RSC, at a given time.

FIG. 4 is a graph illustrating the non-dimensional temperature measured by the heat flux probe 10 by each thermocouple 24, 26 and 28 at two different elevations within the RSC 100, at two different times. As shown in FIG. 4, the measured temperature from each thermocouple 24, 26 and 28 at the two different elevations is a substantially linear relationship. Thus, the measured temperature from each thermocouple 24, 26, 28 at each of the different elevations could be linearly extrapolated to yield the back side and front side temperatures. A small variation in the back side temperature verified that the extrapolated backside temperature is constant with time and independent of the elevation of the heat flux probe 10, and therefore the heat flux probe 10 can determine a fouling thickness within the RSC 100 based on a measured heat flux because the variation in heat flux is due only to the events at the front side of the probe 10.

The measured heat flux from the probe 10, which is exposed to the syngas at the front side and to the water at the backside is given as follows:

$$Q_{meas} = Q_{rad} + Q_{conv}$$
$$= Q_{cond} = -K(T)\frac{dT}{dx}$$
$$= h_{eff}(T_{gas} - T_{surf})$$

For clean surface the measured heat flux is given by:

$$Q_{meas,clean} = \frac{T_{gas} - T_{metal,clean}}{1/h_{eff} + K_{metal}/L_{metal}}$$

For a fouled surface the measured heat flux is:

$$Q_{meas,fouled} = \frac{T_{gas} - T_{metal,fouled}}{1/h_{eff} + K_{metal}/L_{metal} + K_{fouling}/L_{fouling}}$$

Figure 5:
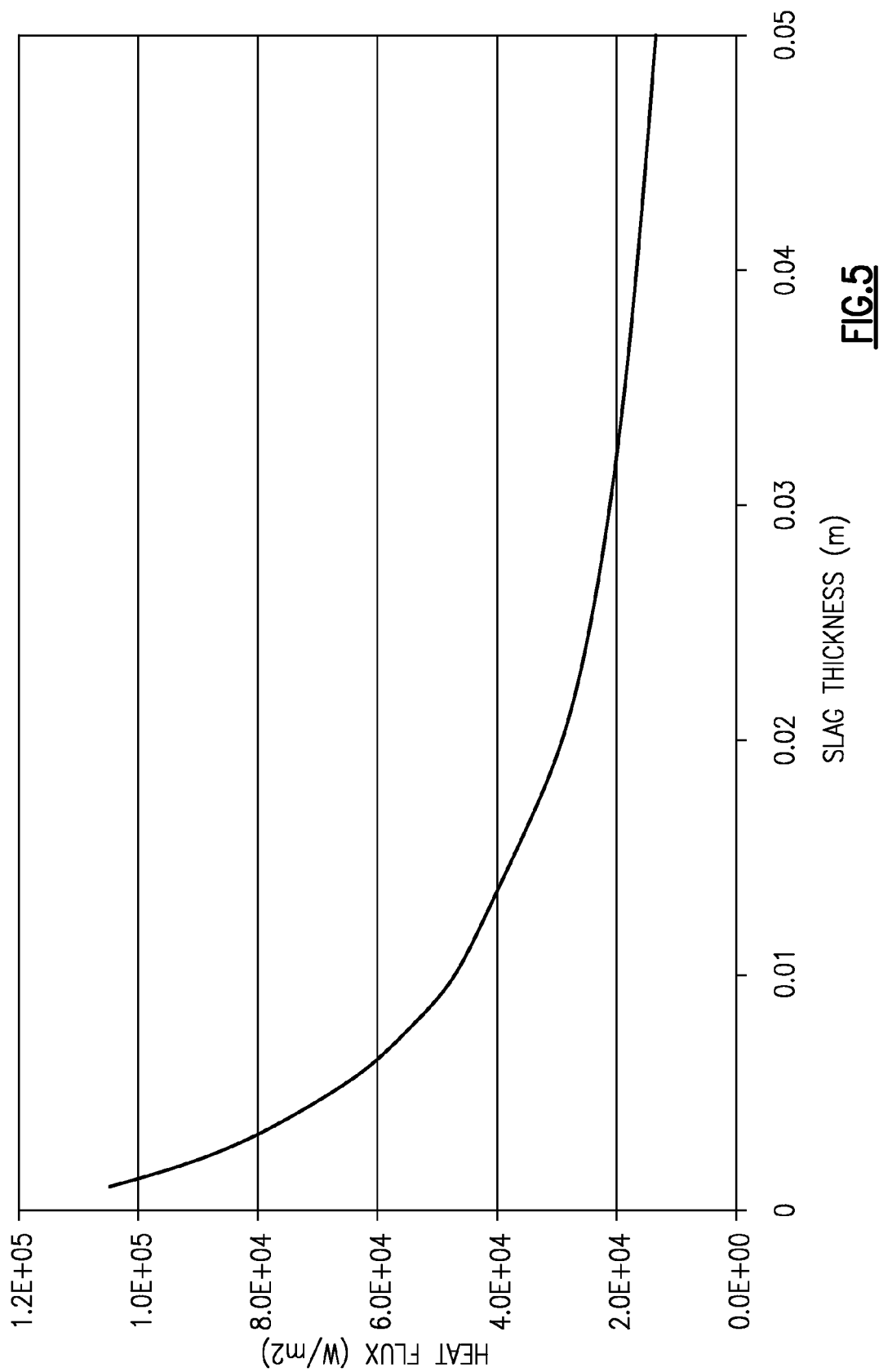
FIG. 5 is a graph illustrating an example of correlation between the heat flux and the fouling thickness on the wall of the RSC.

Based on the assumption that the syngas heat transfer coefficient and the gas temperature are substantially constant and using the equations above, an algorithm was developed that provides a correlation between the measured heat flux and the fouling thickness, as shown in FIG. 5. As is known in the art, the algorithm can reside, for example, in a CPU of a controller, and the like. The gas temperature was evaluated based on prediction models and thermocouple measurements. As shown in FIG. 5, the heat flux is reduced by about 50%, for example, when the fouling thickness is estimated to be about 0.24 inches.

Feasibility studies so far have demonstrated that the heat flux probe of the invention could be used to estimate a fouling thickness in the RSC 100. The results of the feasibility study proved that the measured heat flux from the heat flux probe 10 decreases with time as fouling thickness increases, thereby providing an accurate estimation of fouling thickness over a period of time.

As described above, the temperature measurements from the three thermocouples 24, 26, 28 proved that the back side temperature could be linearly extrapolated. Therefore, the principles of the invention can be applied to a heat flux probe using two thermocouples, rather than three thermocouples, to measure temperature at the outer surface and inner surface of a tube, for example, a water tube. In this embodiment, a first thermocouple measures the relatively hotter temperature at the outer surface of the wall, while the second thermocouple measures the relatively cooler temperature at the inner surface of the wall. For example, the outer surface of the wall may be proximate the hot syngas, while the inner surface of the wall may be proximate the water passing through the tube. It will be appreciated that a plurality of heat flux probes could be located at a plurality of locations along the length of the tube.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A heat flux measurement device for estimating a fouling thickness on a wall whose fouling thickness is of interest, comprising:
    a front portion having a front wall and a cavity, the front wall being positioned proximate a wall whose fouling thickness is of interest;
    a first thermocouple disposed within the front portion at a first distance from the front wall for measuring a first temperature of the front portion;
    a second thermocouple disposed within the front portion at a second distance from the front wall for measuring a second temperature of the front portion,
    wherein a temperature of the front wall is determined by linearly extrapolating the first and second temperatures using an algorithm residing on a central processing unit, and
    wherein a variation of heat flux is determined using the temperature of the front wall and the algorithm residing on the central processing unit, and
    wherein a fouling thickness on the wall whose fouling thickness is of interest is estimated by using the algorithm residing on the central processing unit that correlates the variation of heat flux as a function of fouling thickness.

2. A device according to claim 1, further comprising a coolant disposed in the cavity of the front portion.

3. A device according to claim 1, further comprising a third thermocouple disposed in the front portion at a third distance from the front wall for measuring a third temperature of the front portion over a period of time.

4. A device according to claim 3, wherein the first, second and third thermocouples are located at a distance of about 0.10 inches, about 0.20 inches and about 0.40 inches from the front wall, respectively, or at any other distance from each other.

5. A device according to claim 1, wherein the first and second thermocouples are radially offset from each other with respect to a central, longitudinal axis of the device.

6. A device according to claim 1, wherein the wall whose fouling thickness is of interest comprises a water wall of a radiant syngas cooler (RSC).

7. A method of estimating a fouling thickness on a wall whose fouling thickness is of interest using a heat flux measurement device, the heat flux measurement device including a front portion having a front wall, a first thermocouple disposed within the front portion at a first distance from the front wall, and a second thermocouple disposed within the front portion at a second distance from the front wall, the method comprising the steps of:
    measuring a first temperature of the front portion using the first thermocouple;
    measuring a second temperature of the front portion using the second thermocouple;
    determining a temperature of the front wall by linearly extrapolating the first and second temperatures using an algorithm residing on a central processing unit;
    determining a variation of heat flux using the temperature of the front wall and the algorithm residing on the central processing unit; and
    estimating a fouling thickness on the wall whose fouling thickness is of interest by using the algorithm residing on the central processing unit that correlates the variation of the heat flux as a function of fouling thickness.

8. A method according to claim 7, wherein the wall whose fouling thickness is of interest comprises a water wall of a radiant syngas cooler (RSC).

* * * * *